(12) United States Patent
Marquant et al.

(10) Patent No.: US 8,398,845 B2
(45) Date of Patent: Mar. 19, 2013

(54) ANALYSIS DEVICE WITH REPLACEABLE TEST FIELD SUPPORT

(75) Inventors: Michael Marquant, Mannheim (DE); Mihail-Onoriu Lungu, Schwegenheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1216 days.

(21) Appl. No.: 11/872,506

(22) Filed: Oct. 15, 2007

(65) Prior Publication Data
US 2008/0078680 A1 Apr. 3, 2008

Related U.S. Application Data

(63) Continuation of application No. PCT/EP2006/061449, filed on Apr. 7, 2006.

(30) Foreign Application Priority Data

Apr. 14, 2005 (DE) .......................... 10 2005 017 364

(51) Int. Cl.
*G01N 27/327* (2006.01)
*G01N 27/416* (2006.01)
(52) U.S. Cl. ................ 205/792; 205/777.5; 204/403.01; 204/400; 422/82.01
(58) Field of Classification Search .................. 204/403.01–403.03, 406, 400; 205/777.5, 792; 422/82.01
See application file for complete search history.

(56) References Cited

U.S. PATENT DOCUMENTS

| | | | | |
|---|---|---|---|---|
| 4,963,245 A | * | 10/1990 | Weetall | 506/9 |
| 5,047,044 A | | 9/1991 | Smith et al. | |
| 5,286,362 A | | 2/1994 | Hoenes et al. | |
| 5,352,351 A | * | 10/1994 | White et al. | 204/403.04 |
| 6,027,689 A | | 2/2000 | Markart | |
| 6,117,289 A | * | 9/2000 | Yamamoto et al. | 204/403.08 |
| 6,132,683 A | | 10/2000 | Sugihara et al. | |
| 6,140,045 A | | 10/2000 | Wohlstadter et al. | |
| 6,187,164 B1 | | 2/2001 | Warren et al. | |
| 6,428,664 B1 | * | 8/2002 | Bhullar et al. | 204/403.03 |
| 6,488,828 B1 | * | 12/2002 | Bhullar et al. | 204/403.01 |
| 6,743,635 B2 | * | 6/2004 | Neel et al. | 436/95 |
| 2003/0070917 A1 | | 4/2003 | Giaquinta et al. | |
| 2004/0194295 A1 | | 10/2004 | Green | |
| 2005/0230253 A1 | | 10/2005 | Marquant | |

FOREIGN PATENT DOCUMENTS

| | | |
|---|---|---|
| DE | 195 46 535 | 6/1997 |
| GB | 2 386 949 | 10/2003 |
| WO | WO 90/13017 | 11/1990 |
| WO | WO 2004/030822 | 4/2004 |

* cited by examiner

*Primary Examiner* — Alex Noguerola
(74) *Attorney, Agent, or Firm* — Bose McKinney & Evans LLP

(57) ABSTRACT

A measuring device for analyzing a sample liquid having at least one analyte is provided. A test field support housed in the device includes a number of individual test fields in communication with electrochemical measuring cells of the test field support. Reagents can be assigned to the electrochemical measuring cells which can react with a sample liquid. The reaction can lead to a measurable change of at least one quantity characteristic of the presence or concentration of an analyte in the sample. The measuring device includes evaluation electronics. The individual test fields on the test field support are accessible to the user after the measuring device has been opened.

28 Claims, 10 Drawing Sheets

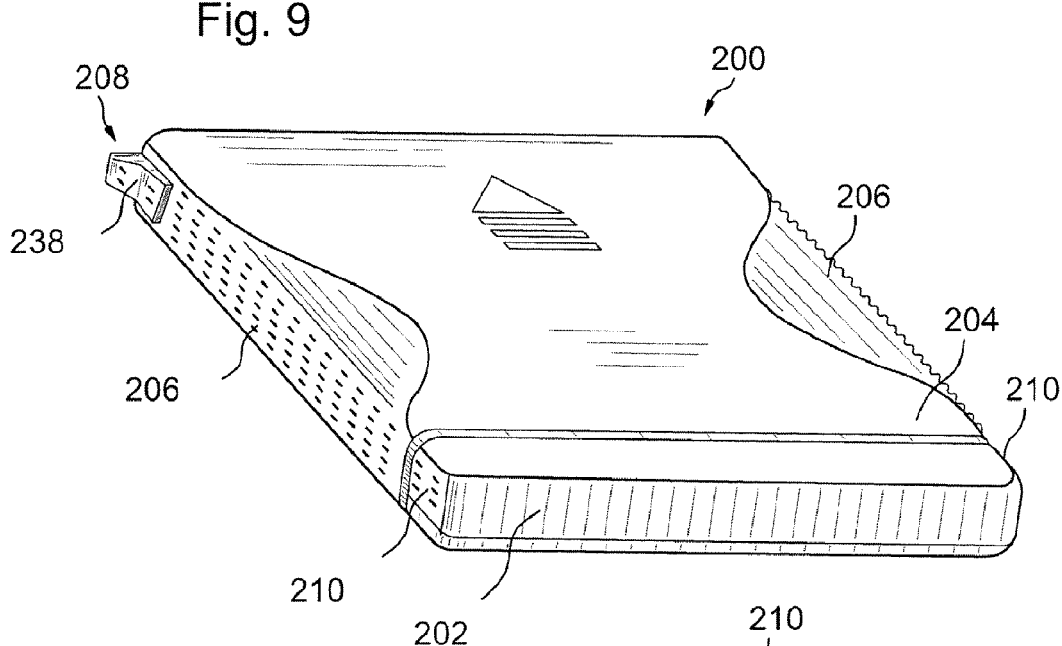
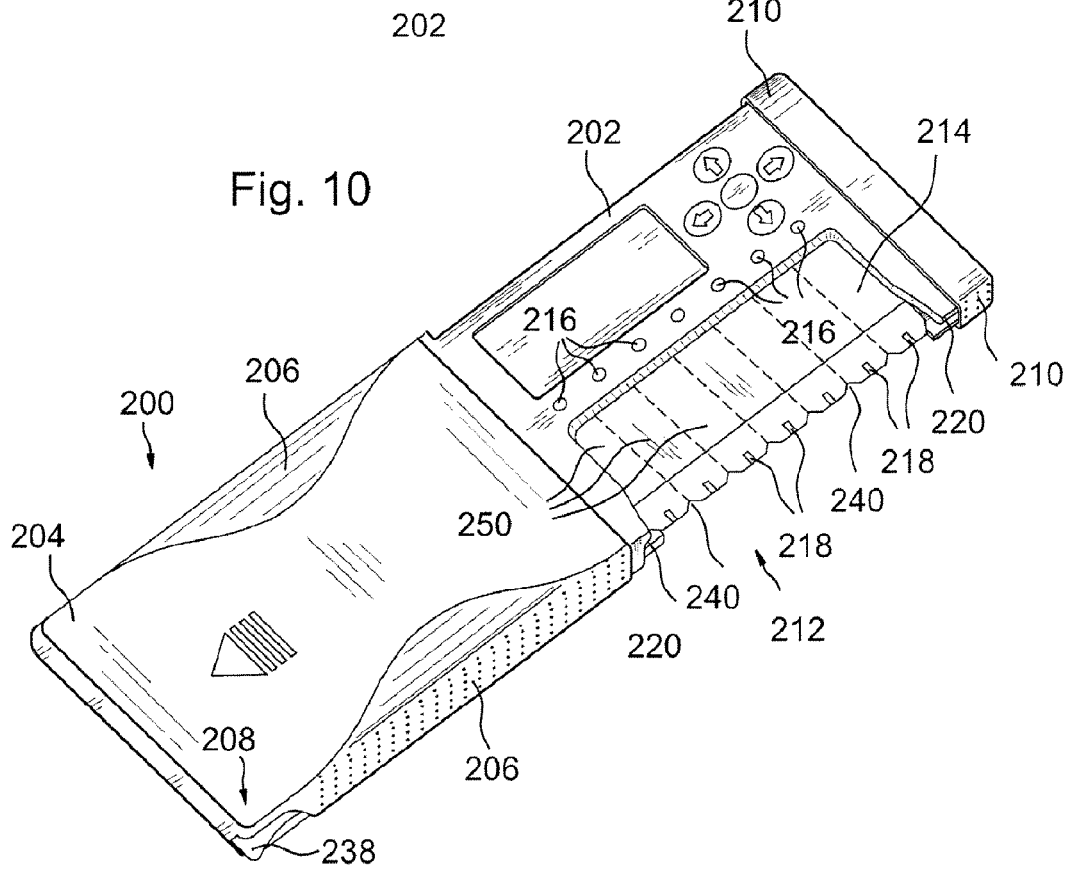

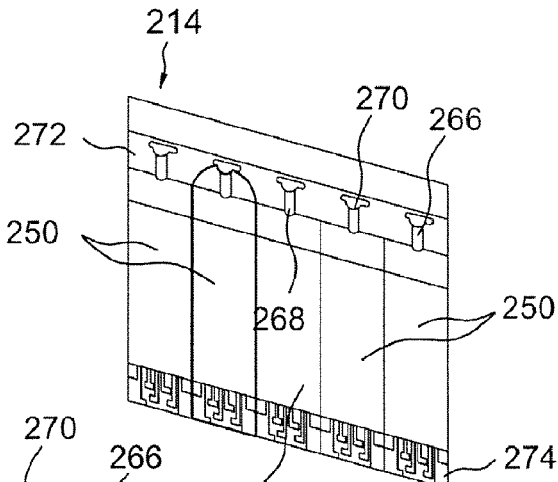
Fig. 14A
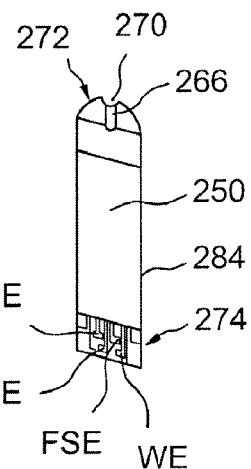
Fig. 14B
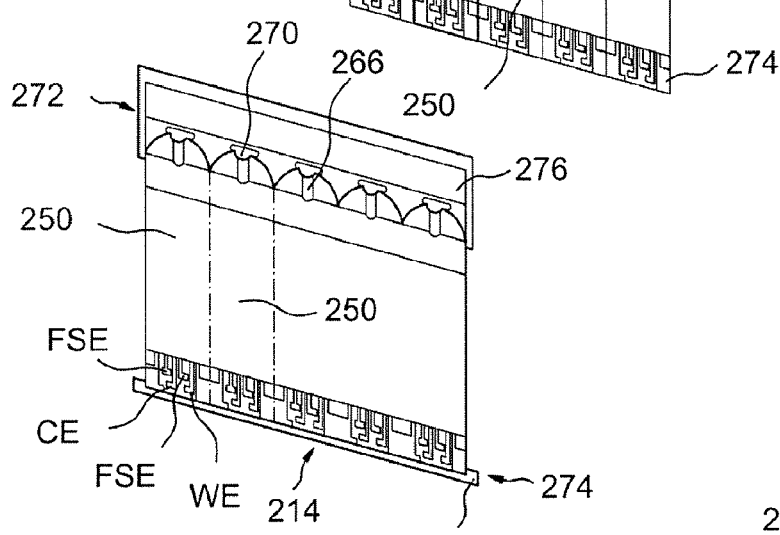
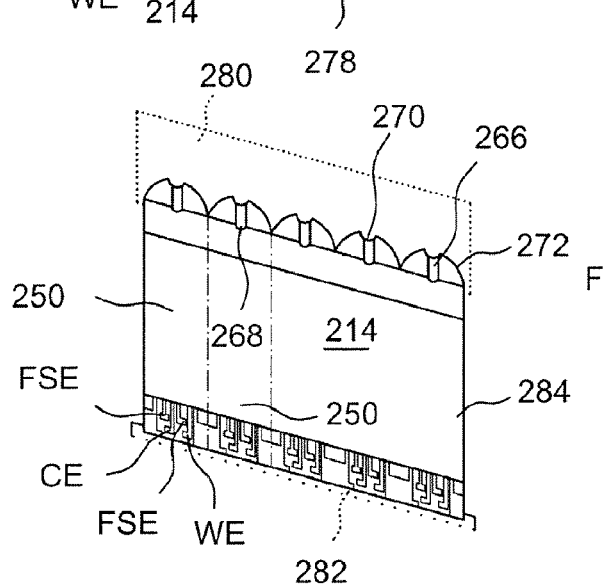
Fig. 14D
Fig. 14E

ANALYSIS DEVICE WITH REPLACEABLE TEST FIELD SUPPORT

RELATED APPLICATIONS

This application is a continuation application of International Application PCT/EP2006/061449, filed Apr. 7, 2006, which claims priority to DE 10 2005 017 364, filed Apr. 14, 2005, which are hereby incorporated by reference in their entirety.

BACKGROUND

The invention relates to an analysis device for the determination of concentration or presence of an analyte in a human body fluid, and more particularly, a device of this type that can be used several times in succession.

U.S. Pat. No. 5,286,362 discloses a method and a sensor electrode system for electrochemical determination of an analyte or of oxidoreductase, as well as suitable substances for the electrochemical determination. Electrons are transferred in the presence of an oxidoreductase and a reducible substance, and are transferred in the course of the determination reaction from the oxidoreductase to an electrode. This produces a signal which allows determination of the analyte, the reducible substance being enzymatically reduced and oxidized at the electrode. The substance which is produced at the electrode by oxidation differs from the reducible substance originally used. A corresponding sensor electrode system and components suitable for it are furthermore disclosed. According to U.S. Pat. No. 5,286,362, a mixture of an oxidoreductase and a first reducible substance is used. The first reducible substance is reduced by the oxidoreductase and produces a reduced substance in an irreversible reaction. This reduced substance is oxidized to produce a second reducible substance which differs from the first reducible substance. Instruments are provided for holding the mixture of the oxidoreductase and the first reducible substance as well as for bringing the mixture in contact with a liquid sample which may contain the analyte. Contact instruments are also provided for electrical connection of the mixture upon contact with the sample to two electrical leads that are physically separate from each other. The contact instruments enclose an electrically conductive surface for receiving the electrodes from the first reducible substance when the first reducible substance is reduced by the oxidoreductase and the reduced substance is produced, and for oxidizing the reduced substance at the electrically conductive surface to form the second reducible substance.

U.S. Pat. No. 6,027,689 discloses a test card for optical or electrical determination of the concentration of a substance in a liquid. The test card is used in a measuring device for evaluating the concentration of a substance in a liquid such as body fluid. The test card has layers of material that are suitable for being united in a continuous process during which the layers are unrolled from corresponding storage rolls. Each test card comprises a number of individually usable test sections that are joined together and arranged in a successive sequence along the length of the test card. The material layers of the test card cooperate to define at least one reaction layer and a cover layer covering it, the cover layer comprising an opening for receiving a sample drop in each test section. A distribution layer and a carrier material layer can likewise be incorporated in the test card, the carrier layer in each test section comprising a measurement opening which coincides with the opening for the sample drop. Weakened zones are provided in the material between neighboring test sections, allowing simple removal of a used test section from the remaining unused test sections.

WO 2004/030822 discloses a multiple capillary sensor analysis system used to analyze a sample liquid for an analyte, in particular, for analyzing a human or animal body fluid. A capillary sensor is provided that includes a capillary channel enclosed by at least two wall parts and having an inlet opening for the sample liquid and a vent opening. The capillary channel contains reagents that react with the sample liquid, thereby causing a change in a parameter that can be measured. An evaluation device is provided that has a capillary sensor frame for positioning a capillary sensor in a measuring position in order to carry out an analysis. The capillary sensor is positioned such that the inlet opening of the capillary channel is accessible for contact with a liquid sample to be studied, the liquid sample entering and filling the capillary channel due to capillary forces. Measurement and evaluation electronics are also provided to measure the parameter and correlate it to the information being sought, e.g., glucose concentration of the liquid sample. The capillary sensors are provided as multiple capillary strips with successively arranged capillary sensors. A multiple capillary sensor strip is guided and held in the capillary sensor frame of the evaluation device so that one capillary sensor of the strip lies in the measuring position and its inlet opening is accessible for contact with sample liquid. The multiple capillary sensor strip can then be moved in the evaluation device to transport consecutive capillary sensors of the sensor strip to the measuring position. The evaluation device comprises a cutting instrument which, after carrying out each measurement, cuts the capillary sensor used for the measurement from the multiple capillary sensor strip. Capillary sensors of the multiple capillary sensor strip are provided as electrochemical capillary sensors, each of which have a working electrode, a counter electrode and sensor contacts which are connected to the electrodes via conductor tracks and are in contact with corresponding device contacts of the evaluation device during the measurement to electrically connect to the measurement and evaluation electronics.

The above-discussed references describe arrangements of test field supports in which a plurality of individual test fields are arranged in a row on a band or a bar, and a new test field must be transported to the sample application position each time a new test is performed. The references teach that the successively used individual test fields are removed. Transporting a test cell or test section to a fixed application position in the device entails relatively high outlay, which is inherent to all the above-discussed references. The user of the above-discussed arrangements is offered only one test section at a time, the test section being arranged on a band-shaped or strip-shaped support. The user is thus restricted in terms of selection, and can use only the test section that is currently positioned in the application position.

SUMMARY OF THE INVENTION

Embodiments incorporating the present invention address the disadvantages of the prior art and the problems mentioned above.

One embodiment provides an analysis unit which allows simplified handling by an end-user, for example a diabetic, and is constructed more simply. A plurality of individual test fields or test sections are arranged in the form of a matrix on a test field support, so that the individual test fields can be used in any order, which can be arbitrarily selected by a user. According to other embodiments, the position of the individual test fields on the test field support, and therefore the position of the individual test fields with respect to the measuring system, is fixed. It is therefore possible to apply the sample at any of the available different positions of the individual test fields. The transport of a test field to a fixed application position, which can only be carried out with considerable expense, is therefore not required. This greatly simplifies the structure of the measuring device.

In contrast to using an individual test field support for each test field, the amount of handling can be significantly reduced by using a test field support having a plurality of individual test fields. The plurality of individual test fields can be arranged in a matrix on a side of the test field support accessible to the user. The number of individual test fields arranged on a single test field support can be adapted, e.g., to the number of glucose measurements required over a day by a diabetic, and the test field support can be replaceable. This arrangement considerably simplifies carrying out a single measurement and also avoids the need to dispose of individual used test strips or individual test fields after each test is conducted. This is in contrast to the above-described references that require individual test strips to be disposed of once used and also be separated from a continuous material.

In contrast to individual test fields or bars arranged in row form on bands that are transported through an analysis unit as described above, the embodiments disclosed herein avoid complex mechanical or electromechanical drives, which take up installation space, as well as the transport mechanisms necessary for them. The analysis units or analysis systems can therefore be much smaller, in particular, much flatter. Avoiding mechanical or electromechanical drives and transport mechanisms also makes it possible to produce such analysis units at much lower costs. Embodiments of the analysis units taught herein are less susceptible to malfunction and, compared with systems in which electrical drives are used, consume less power. Battery life will thus be longer, and smaller, less expensive batteries can be used.

Embodiments of the analysis units having test field supports configured to be replaceable enable successive determination of the same parameter of a sample by use of the individual test fields arranged on the replaceable test field support.

One embodiment provides an analysis unit having simplified handling. An electrical contact between the analysis unit and the test field support, which can be removably and replaceably inserted into the unit, can be established when the test field support is inserted into a housing depression or a differently configured housing facility. The electrodes of the electrochemical measuring cells of the individual test fields of a test field support can be connected simultaneously to a common electrical measurement and control circuit. The analysis unit can automatically detect which of the individual test fields on the test field support have recently been used. Interconnection of the individual test field recently used takes place electronically with the measurement and control circuit of the analysis unit to carry out the determination measurement. The individual test fields can be arranged on the test field support in the form of a matrix. After all the individual test fields of a given test field support have been used, the test field can be removed from the analysis unit and replaced with a new test field support.

In another embodiment, the analysis unit having a replaceable test field support can be configured in the form of a fold-down case having an upper shell and a lower shell. In a housing depression or cavity formed on the lower shell, a substantially flat test field support (e.g., credit card shaped) having individual test fields can be inserted. After insertion, an electrical contact strip formed on the rear side of the test field support mates with and is electrically connected to an electrical contact strip formed on the lower shell's rear side. The electrical contact strip can be located in the housing depression in the lower side of the analysis unit which is provided in the form of a case. According to this embodiment, several individual test fields are arranged in a matrix on the upper surface of the test field support which is accessible to the user after opening the upper shell.

In one embodiment, the test field support includes a support sheet on which at least two electrodes are formed at individual test field positions by methods such as laser ablation, lithography or screen printing. The support sheet includes a sufficient amount of rigidity or stiffness to support test fields or electrodes. These test fields and/or electrodes are connected by conductor tracks to electrical contact surfaces at the edge of the test field support. A reagent layer is applied over the surface of the base sheet at least partially onto the electrode and/or conductor track structures. The reagent layer can handle the reagents necessary for specific detection and measurement of the intended parameters from the sample. A spacer sheet located on the reagent layer can be, for example, adhesively bonded onto the reagent layer. The spacer sheet includes holes at the positions of the electrodes to form measuring chambers. A cover sheet is furthermore applied on the spacer sheet. The cover sheet can, for example, be adhesively bonded onto the spacer sheet and seals the measuring chambers. Openings are included to receive the sample at the measuring positions and to provide a vent hole. A sealing sheet is provided above the cover sheet to externally seal the capillary spaces in a substantially moisture-tight fashion.

In order to carry out the measurement, one of the measuring chamber dosing openings is opened by the user. A ring-pull closure, a tab, or the like is provided for this purpose. A sample can then be applied to the measuring chamber for measurement.

Before the first individual test field on the test field support can be used for the measurement, the test field support is inserted into a measuring device. The measuring device is provided in the form of a case including an end having an indentation, recess or cavity. In order to insert the test field support and to carry out a measurement, an upper shell of the case of the analysis unit is folded open. The case can include a display on its inside that the user can read when it is open. The test field support is then inserted into the recess or depression in the lower shell. After the measurement, the analysis unit can be deactivated by folding the upper shell to close the cases. Activation of the analysis unit can be carried out by folding the upper shell open.

The electrodes of the individual test fields arranged on the upper side of the test field support can be simultaneously connected to the contacts of the analysis unit. A measuring cell can be selectively electrically connected to the measurement and control circuit of the device using an analog semiconductor switching matrix. After the analysis unit is activated, the measuring electrodes of the individual test fields can be serially electronically tested by a conductance measurement. The analysis unit can detect which of the individual test fields has been dosed with a sample, and then can carry out the electrochemical detection measurement on the corresponding electrodes. The result can be subsequently shown on the display located inside the upper shell.

Another embodiment includes a test field support having a continuous band of capillary sensors. According to this embodiment, the individual capillary sensors are not cut into individual test strips, but are instead grouped together in blocks in a mutually adjacent or side by side arrangement to form a plurality of capillary sensors. The continuous band can be constructed from individual layers of materials held on a plurality of rolls. Such a band can include a plurality of layers. These multiple layers are sandwiched together and cooperate to define multiple electrochemical measuring cells, each having a sample receiving opening and a capillary channel configured to draw sample fluid into the measuring cell. Each sensor includes a base sheet in the form of a strip includes a conductive structure, an electrode surface, conductor tracks and contacts. A strip-shaped reagent film with the reagents necessary for the intended detection reaction can be applied onto a stiffer base sheet in the region of the electrodes. On this reagent film, a stamped spacer sheet forms a capillary and a measuring cell above the electrode surface on one side of the band. On the other side of the band, contact surfaces for electrical connection at the ends of the conductor tracks are exposed. A cover sheet which seals the capillaries on the upper side and forms a vent hole at the inner end of the capillary is adhesively bonded onto the spacer sheet for closure. A moisture-isolating seal can be used to protect the reagent layer. In this event, the band can be formed longer in front of the capillary side. In this case, a U-shaped stamping region around the front of the capillary can leave the capillary open on the dosing side, but simultaneously form a closed frame around the dosing opening. By sealing around the stamped region with a vapor-tight sheet, the capillary region with the reagents provided can be substantially protected against ingress of moisture. In order to expose the capillary opening, the frame can be bent down on the front edge so that a protective sheet can be removed from the dosing opening.

Two band-shaped sections having layers are inserted opposite each other into an analysis unit. The sections can include, for example, five individual test fields, such as five capillary measuring cells. The analysis unit includes a lower part having a block-shaped test field support respectively placed on two opposite sides thereof. An upper part is connected to the lower part of the analysis unit by a hinge. The upper part is folded onto the lower part after insertion of the test field supports which fixes the test field supports inserted into the analysis unit. At the same time, resilient contacts arranged in a row correspondingly contact the measuring cell electrodes with electronics in the upper part.

A display can be located on the upper side of the folded-shut device. Control buttons can be provided on the upper side. The analysis unit according to this embodiment can include openings for the sample application positions, i.e., the capillary openings of the block-shaped test field supports inserted into the analysis unit, which face out on both sides and are therefore readily accessible.

The analysis unit may furthermore include an outer cover sleeve which can be slid over the analysis unit. In this position, the cover sleeve can form a handle for holding the analysis unit. Also, according to this alternative embodiment, the electrodes of the individual test fields of the test field support are simultaneously connected to the contacts of the analysis unit. An individual measuring cell can be selectively connected to the measurement and control circuit of the device electronically, for example, using an analog semiconductor switching matrix as discussed above. After the analysis unit is activated, the measuring electrodes of the individual test fields can be electronically tested in series by a conductance measurement. The analysis unit or a measuring algorithm implemented in the unit detects which of the individual test fields has been dosed with a sample. An electrochemical detection measurement can then be carried out, and the result subsequently shown on the display of the analysis unit. After all the individual test fields of the test field support have been used. The block or card including test fields can be removed from the analysis unit by folding open the unit.

According to another alternative embodiment, a test field support can be slid into a module including a slot. The module including the slot can be slid into a complementary sleeve to be securely held thereby. The module includes, for example, a rectangular recess into which the card-shaped test field support containing a plurality of individual test fields can be inserted. Individual test fields or test sections, each have portions extending from a line, such as in the form of tongues, and have capillary openings on an outer edge thereof.

The individual test fields or test sections can be in a mutually adjacent, i.e., side by side, arrangement. A light-emitting diode can be assigned to each individual test field. After having used all the individual test fields of a test field support card, the used test field support can be removed by unlatching on the card from the module. A new test field support having unused individual test fields or test sections can be inserted into the slot in the module.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIG. 9 is a perspective view of another embodiment of an analysis unit;

FIG. 10 is a perspective view of the analysis unit of FIG. 9 shown with the module partially removed from a box and with a card-shaped test field support inserted;

FIGS. 14A to 14E are perspective views of a test field support in the form of a card having individual test strips, with and without a protective sheet in the region of the terminal electrodes and in the region of the capillary openings.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The terms "measuring devices" or "analysis units" include portable devices which a user can carry with them on their person. Such transportable measuring devices or analysis devices can contain a long-term energy storage device to supply energy to evaluation electronics of the portable measuring devices or the portable analysis unit. The test field supports, which can be inserted into the portable measuring devices or analysis units, can be a medical consumable material. The test field supports can be removed from the device after use and replaced by new ones. It is also possible, however, to employ multi-use test field supports that can be regenerated after each use so that they can be reused.

Figure 1:
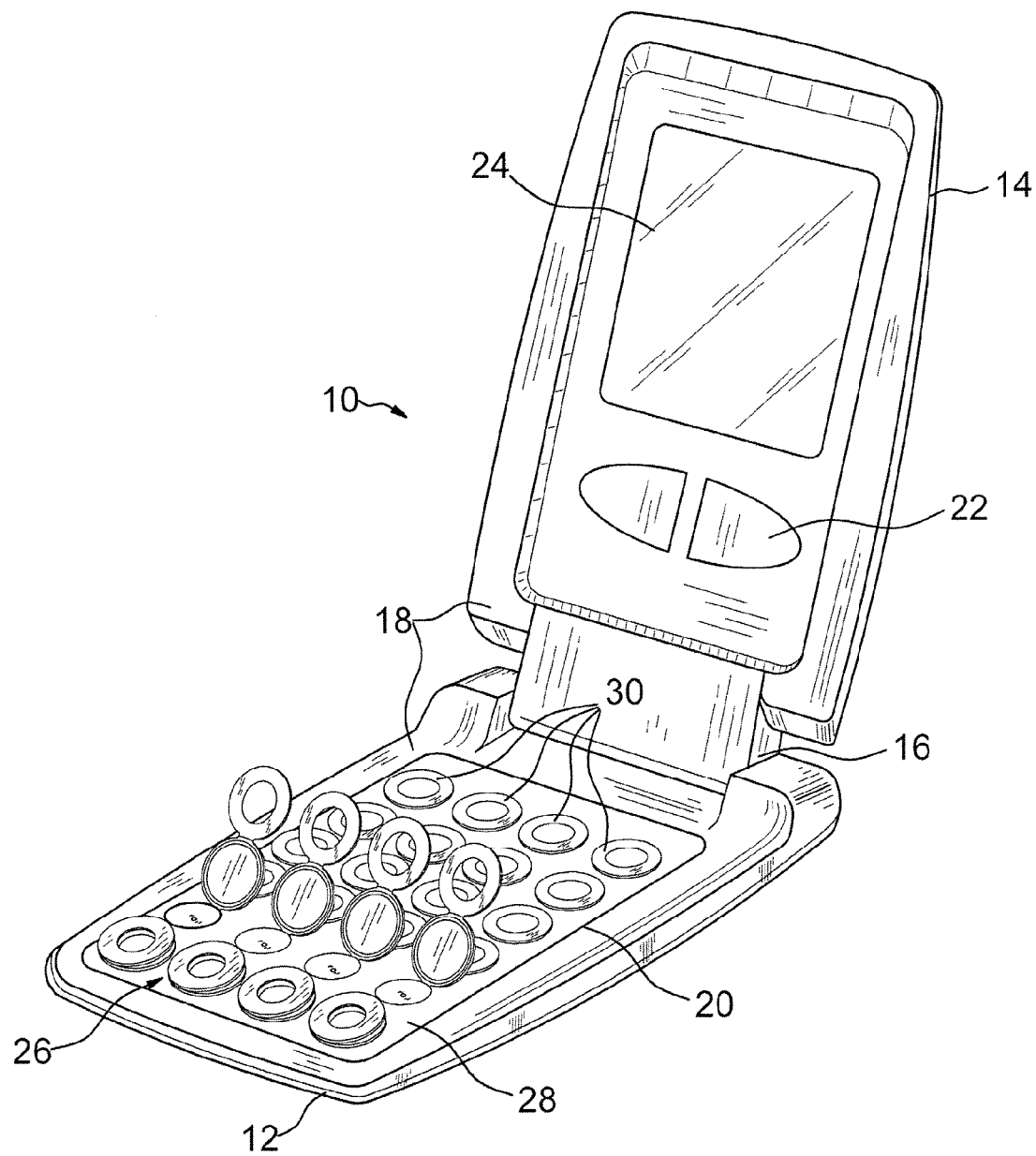
FIG. 1 is a perspective view of an analysis unit having a card-shaped test field support.

FIG. 1 shows an analysis unit having a card-shaped test field support inserted in an analysis unit 10. The analysis unit or measuring device 10 includes a lower shell 12 and an upper shell 14 connected by an articulated connection 16. An indentation in the form of a depression or cavity (see reference number 21 in FIG. 5) is formed in the lower shell 12, into which the flat card-shaped test field support 26 can be inserted. The boundary of the cavity in the lower shell 12 is identified by the reference numeral 20. A first display 22 and a second display 24 are located in the upper shell 14 of the analysis unit 10.

The substantially flat card-shaped test field support 26 includes a test support surface 28 having a test field array 30 arranged in the form of a matrix. After the upper shell 14 of device 10 is opened, the individual test fields of the test field array 30 are accessible. Each individual test field of the test field array 30 is initially closed, and can be opened by a user as will be described in more detail below.

After the upper shell 14 is opened, the user can select any of the individual test fields of the test field array 30. For diabetics, for example, the device provides a simple and user-friendly procedure since the number of blood sugar measurements required daily for diabetics can be carried out simply with the individual test fields. Once a corresponding individual test field from the test field array 30 has been used, it can remain inside the test field support 26. The environmental burden resulting from discarded test strips which occurs in other devices can be avoided or at least delayed.

Figure 2A:
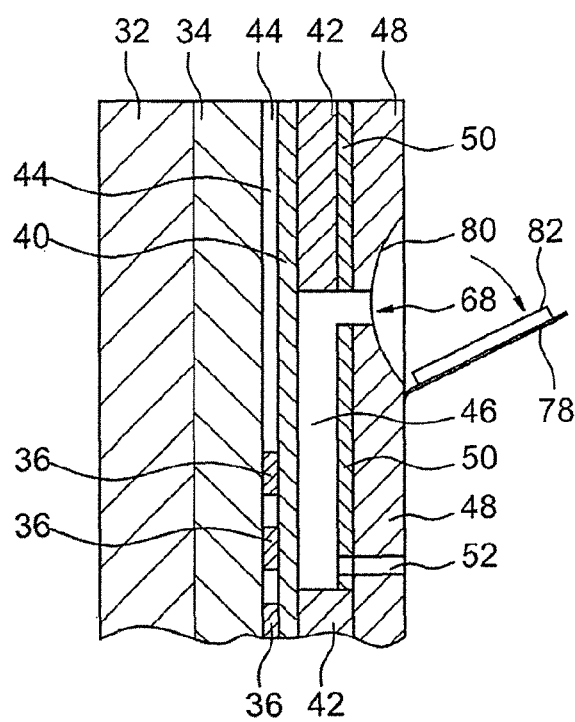
FIG. 2A is a cross-section of the card-shaped test field support shown in FIG. 1.

It can be seen from the sectional representation of FIG. 2A that the test field support 26 can be substantially flat in the form of a card and can have a layered structure or arrangement. A support sheet 34 is applied onto a base sheet 32 and is covered by a reagent layer 40. A column-shaped hole or void 44 is formed between the support sheet 34 and the reagent layer 40. Conductor tracks 36 for the connection of electrodes 38 (FIG. 2B) extend inside the void 44. The aforementioned reagent layer 40 lies adjacent to or above the conductor tracks 36. Between the reagent layer 40 and a spacer sheet 42 that covers the reagent layer 40 in individual regions, electrochemical measuring chambers or cells 46 (measuring capillary spaces) are formed. The electrochemical measuring cells 46 are covered by a hydrophilic layer 50, which is in turn covered by a cover sheet 48. In order to vent the electrochemical measuring cells 46, both the cover sheet 48 and the hydrophilic layer 50 that is arranged adjacent to or below cover sheet 48 include apertures to provide a vent 52.

The electrochemical measuring cell 46 is formed on a lower side of an individual test field 68 having a reception well 80. A cover or lid 78, which can close and seal the individual test field 68, is shown in its open position in FIG. 2A. On the side facing the reception well 80, the cover 78 includes a sealing edge 82.

Figure 2B:
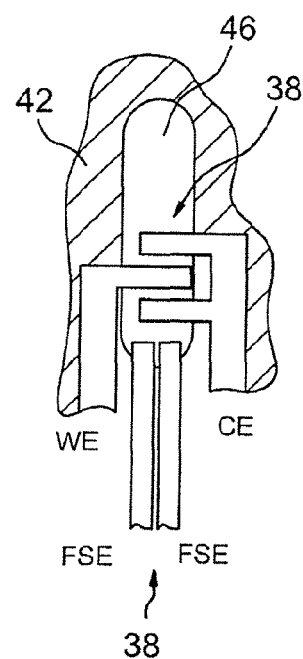
FIG. 2B is a fragmentary plan view in partial cross section of an electrode structure.

As seen in FIG. 2B, the electrochemical measuring cell 46, bounded by the spacer sheet 42, the reagent layer 40 and the hydrophobic layer 50, includes electrodes 38 arranged mutually opposite or side by side. The electrodes 38 include a counter electrode CE and a further electrode WE. The ends of the electrodes CE and WE are interleaved and protrude into each other in the form of a comb. A pair of sample sufficiency electrodes FSE, which can detect the filling level of the electrochemical measuring cell 46, are provided at an individual electrochemical measuring cell 46. The filling level electrodes, FSE, detect the level to which the electrochemical measuring cell 46 is filled with a sample liquid. The electrodes FSE protrude into the electrochemical measuring cell 46 in the region of the electrodes CE and WE.

Figure 3:
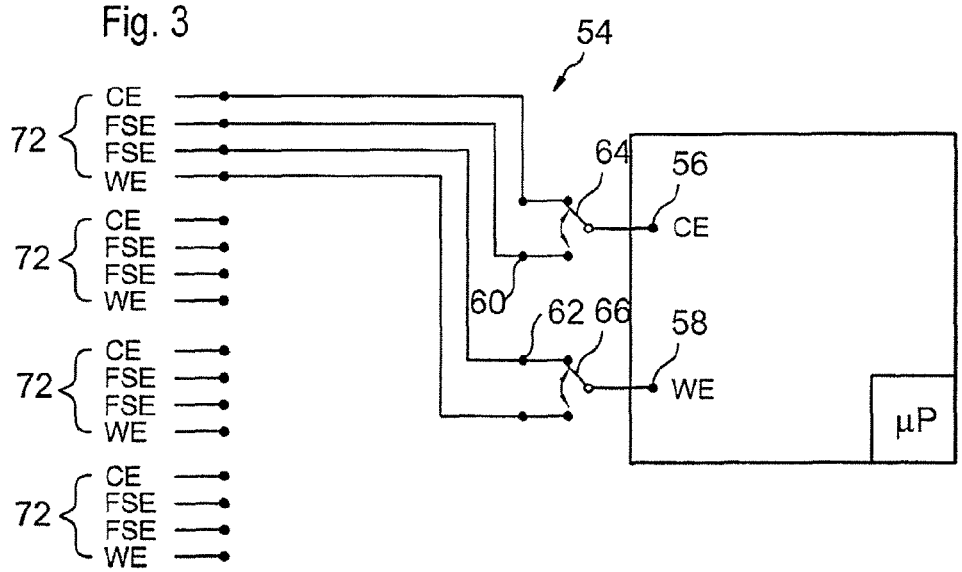
FIG. 3 is a schematic representation of an analog semiconductor switching matrix for electrical contact of the individual fields of the test field support of FIG. 1.

FIG. 3 shows an analog semiconductor switching matrix 54 in a schematic representation. The electrodes 38, CE and WE represented in FIG. 2, as well as the electrodes FSE that detect the filling level of the electrochemical measuring cell 46, are integrated into an analog semiconductor switching matrix 54. Each electrochemical measuring cell 46, and therefore each individual test field 68 of the test field support 26, can include four electrodes. An evaluation component includes a CE terminal 56 that receives a voltage for the CE electrode and a WE terminal 58 that receives a voltage for the WE electrode. Each of the terminals 56, 58 can be coupled to a switch 64 or 66. The first switch 64 switches between the CE electrode and a terminal 60 of the first filling level electrode, whereas the second switch 66 switches between the WE electrode and the terminal of the second filling level electrode 62. This arrangement ensures the particular test field 68 that is wetted by a sample and deliberately selected by the user to be evaluated by the evaluation component which receives voltages conveyed by the electrodes. The result recorded by the evaluation component can be correspondingly shown graphically on the first display 22 or the second display 24. The electrodes CE, WE and the two FSE electrodes can detect the filling level of a body fluid such as whole blood, thinned blood, or plasma in the electrochemical measuring cell 46. These electrodes are assigned to each of the individual test fields 68 in the card-shaped test field support 26. The two filling level electrodes FSE detect the filling level in the electrochemical measuring cell 46 to ensure that a measurement is carried out with a sufficient liquid content in the electrochemical measuring cell 46. The two FSE electrodes also can ensure that both the CE electrode and the WE electrode are fully wetted by the liquid containing the analyte.

Figure 5:
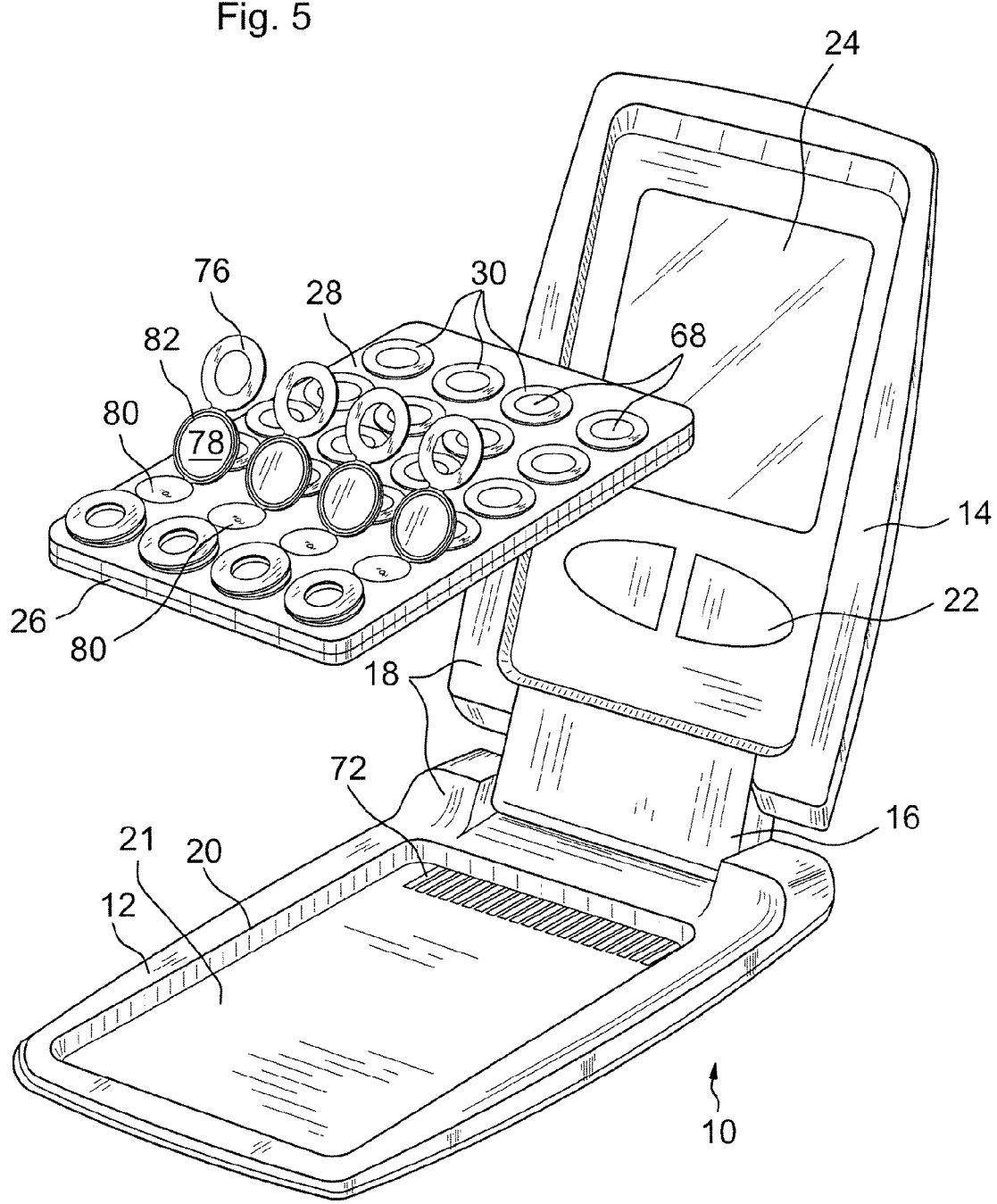
FIG. 5 is a perspective view of an analysis unit having a card-shaped test field support removed from a depression in a lower shell of the analysis unit.

The electrodes CE, WE and the two FSE electrodes are connected to the electrical contact strip 72 which can be located on the shell side as shown in FIG. 5. When the test field support 26 is inserted into the lower shell 12 of the analysis unit 10, the electrical contact strip 72 is connected to a complementarily configured electrical contact strip 70 located on the lower side of the test field support 26. In this way, the individual test fields 68 arranged as a test field array 30 are electrically connected when the test field support 26 is inserted into the lower shell 12. A microprocessor coupled to the analog semiconductor switching matrix 54 switches through the analog semiconductor switching matrix 54 to check to which of the individual test fields 68 an electrically conductive connection has been made. The check is made based on filling the electrochemical measuring cell respectively assigned to this individual test field 68. In order to ensure a reliable measurement result, the filling level of a raw liquid in the relevant electrochemical measuring cell 46 is determined via the FSE electrodes.

Figure 4:
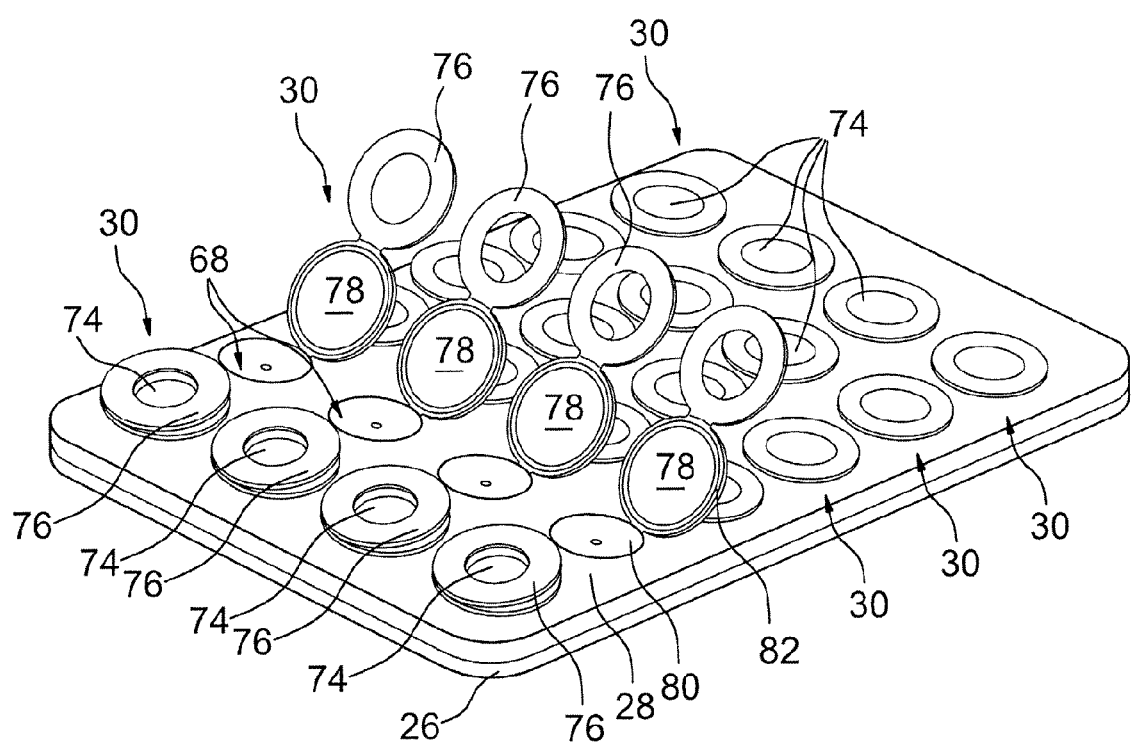
FIG. 4 is a perspective view of a test support showing an upper side of the test support with individual test fields arranged in a matrix with the first individual test field row being open.

FIG. 4 shows an upper side of the flat test field support 26 in the form of a card that can be removed from the depression-shaped indentation in the lower shell 12 of the measuring device 10. In FIG. 2, a majority of the individual test fields 68 in the test field array 30 are closed, whereas one row of the individual test fields 68 is represented in the open state. In the closed state, each individual test field 68 is closed by a cover 78, each of the covers 78 having a sealing edge 82. In the closed state of the cover 78, the sealing edge 82 seals a reception well 80 on the flat test field support 26. In order to open the covers 78, the covers include a ring-pull closure 76, the tab of which protrudes slightly beyond the cover 78 when a reception well 80 is closed by a cover 78. In order to open an individual test field 68 and introduce a body fluid sample, for example, blood, the user pulls on a recloseable ring-pull closure 76 and brings the cover 78 into an upright position as represented in FIG. 4. The ring-pull closure 76 can then be reclosed, so that the individual test field 68 is sealed.

FIG. 5 shows a test field support 26 which is removed and spaced away from the indentation or recess 20 provided in the lower shell of the analysis unit in the folded-open state. FIG. 5 shows the depression-shaped indentation or cavity 21, which is formed in the lower shell 12 of the measuring device 10 delineated by border 20. The replaceable test field support 26 includes individual test fields 68, some of which are accessible because the cover 78 is open. The majority of the individual test fields 68 formed on the upper side of the flat test field support 26 are shown as sealed by closed covers 78. The electrical contact of the flat test field support 26 is made by a contact strip 72 formed in recess 21 contacting a complementary electrical contact strip formed on the lower side of the test field support 26. Thus, when the test field support 26 is inserted into the cavity of the lower shell 12, contact with the flat test field support 26 takes place directly.

Figure 6:
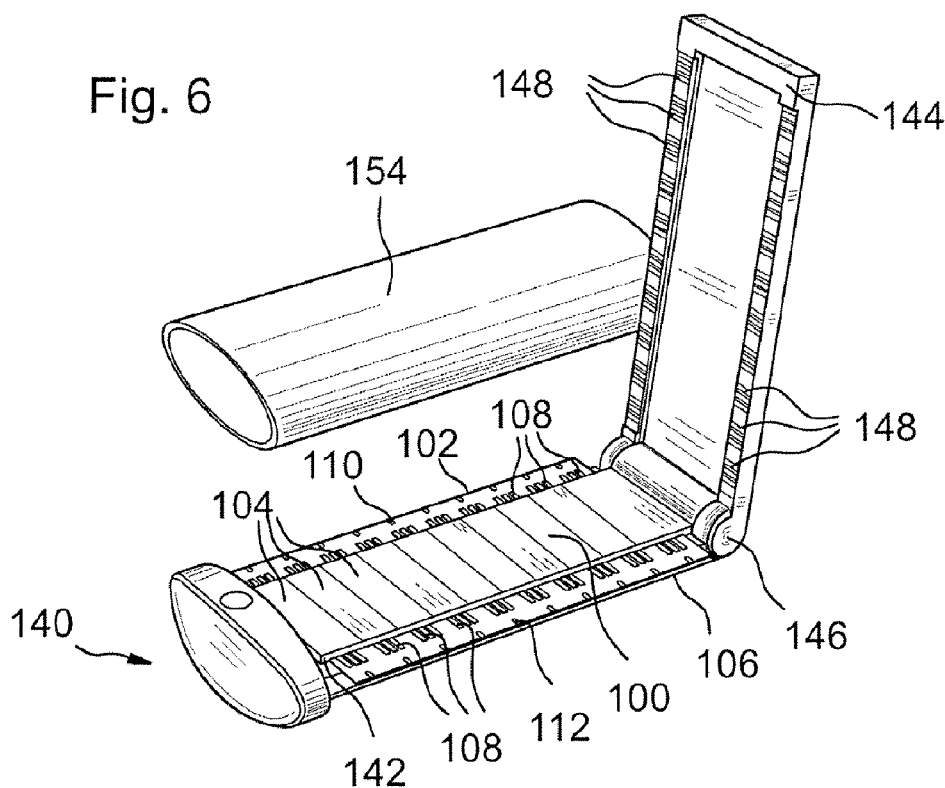
FIG. 6 is a perspective view of another embodiment of an analysis unit shown folded open.

FIG. 6 shows another embodiment including a lower part 142 and an upper part 144 connected together at a hinge 146 and a corresponding measuring device or analysis unit 140 in the open state. A capillary sensor support 100 can be inserted into the lower part 142 and can include five or more capillary sensors 104 arranged next to one another as shown.

A band assembled from rolls comprises a plurality of layers to create an electrochemical capillary sensor 104 when laminated together. The capillary sensor support 100, containing a plurality of layers in its final assembled state, includes a stiffer base sheet having a conductive structure, electrode surfaces, conductor tracks and contacts. A strip reagent film with the reagents necessary for the intended measurement reaction is applied over the more stiffly designed base sheet by, e.g., flow coating in the region of the electrodes. A further layer is in turn applied on top of the base sheet in the form of a stamped spacer sheet, for example, adhesively bonded. A capillary 108 is located on one side of the capillary sensor support 100. An electrochemical measuring cell is placed over respective electrode surfaces. On the other side of the band a conductor track includes contact surfaces upon which electrical contact can take place. A cover sheet, which seals the capillary 108 at the top and forms a vent hole at the inner end of the capillary 108 is adhesively bonded onto the reagent sheet.

Sealing of the reagent layer against moisture can also be achieved by making the band wider on the capillary side, in which case a U-slot-shaped stamping around the front of the capillary 108 leaves it open on the dosing side. This simultaneously forms a closed frame around the dosing opening. By sealing around the stamped region with a thin vapor-tight sheet, the capillary region with the reagents can be protected against ingress of moisture.

In order to expose the capillary 108, a frame (not shown in FIG. 6) can be bent up on the front edge of the capillary sensor support 100, after which a protective sheet can be removed from the opening of the capillary 108. Two of these sections, for example, each having five individual test fields (capillary measuring cells), can be inserted opposite each other into the analysis unit 140. The lower part 142 and the upper part 144 are closed so that the inserted capillary sensor support 100 can be immobilized. Contact takes place with strip-shaped contact regions 110, 112 of the capillary sensor support 100 so that the measuring cell electrodes can be coupled to electronics, which are accommodated in the upper part 144 of the measuring device 140 by resilient contacts 148 arranged in a row. The two contact regions 110 and 112 extending parallel to one another also run parallel to the first long side 102 or the second long side 106 of the capillary sensor support 100. The electronics test the individual test fields of the capillary sensor support 100. When the capillary sensors 104 have been selected for use by the user, a conductive connection is set up in the assigned electrochemical measuring cell 46 in the capillary sensor 104 being used, due to the sample liquid entering the cell.

Once the upper part 144 of the analysis unit 140 is folded down about the hinge 146, then the contact regions 110, 112 are connected to resilient contacts 148 which are complementarily designed with the profile of the contact regions 110, 112. When the upper part 144 is folded down, an electrical connection is established between the resilient contacts 148 and the contact regions 110, 112 of the capillary sensor support 100. The openings of the capillaries 108 protrude laterally beyond the folded-down upper part 144. The user of the connected capillary sensor support 100 can therefore select which of the capillary sensors 104 is to be used and, in contrast to the solutions known from the prior art, is not restricted to successive presentation of sensors.

Figure 7:
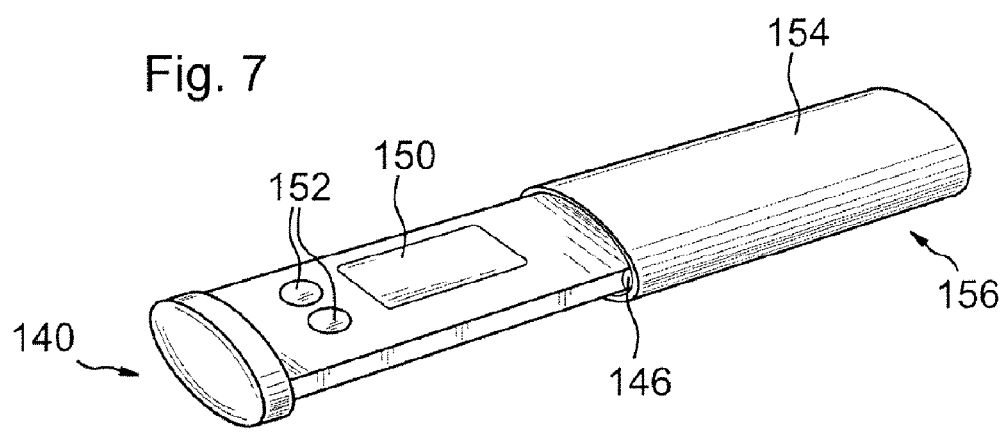
FIG. 7 is a perspective view of the analysis unit of FIG. 6 shown before sliding into a cover sleeve.
Figure 8:
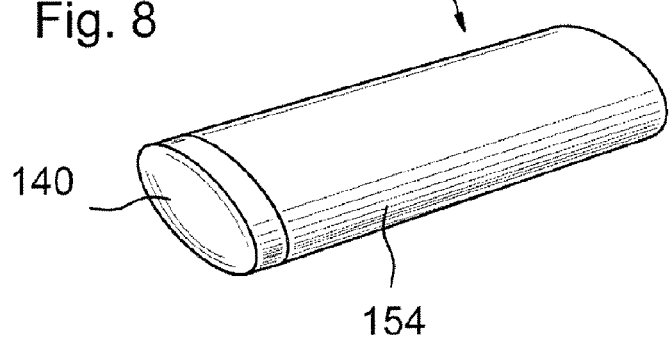
FIG. 8 is a perspective view of the analysis unit of FIG. 6 shown slid into a cover sleeve.

FIG. 7 shows the measuring device 140 folded together, or the analysis unit 140 folded together, before sliding into a cover sleeve. The lower part 142 and the upper part 144 of the measuring device 140 connect with the capillary sensor support 100. The upper side of the upper part 144 includes a display 150 and optional control buttons, which are identified by reference numerals 152. In the folded-together state, the measuring device 140 can be slid into the cover sleeve 154 (See FIG. 8). In the slid-on state 156, the cover sleeve 154 can also be used as a handle for holding the measuring device 140.

The electrodes of the individual test fields or capillary sensors 104 of the capillary sensor support 100 are simultaneously connected to the resilient contacts 148. Determination of the respectively used electrochemical measuring cell for the measurement and control circuit of the measuring device 140 is carried out electronically via an analog semiconductor switching matrix 54 such as depicted in FIG. 3. After activation of the measuring device 140, all of the measuring electrodes of the individual test fields are serially electronically tested repeatedly by a conductance measurement. Consequently, the measuring device 140 detects with the aid of a measurement algorithm, for example, which of the individual test fields has been dosed with a liquid sample. Electrochemical detection measurement is then carried out on the electrodes. The result can be subsequently shown on display 150 on the upper side of upper part 144.

Once all the individual test fields or capillary sensors 104 of the capillary sensor support 100 have been used, the latter is removed from the measuring device 140. The cover sleeve 154 is then slid completely off the measuring device 140. A latch between the upper part 144 and the lower part 142 is then released. After opening the upper part 144 and the lower part 142, the capillary sensor supports 100 can be taken out and replaced by unused, new usable capillary sensor supports 100.

FIG. 9 shows another embodiment module including a slot which can be slid into a box. An arrangement 200 comprises a module 202 including a slot and a box 204 to receive the module 202. Gripping pieces 206 can be externally applied on the box 204. A latching/unlatching device 208 with a latching element 238 is located at one end of the box 204. Gripping surfaces 210 are formed on the extraction side of the module 202 to extract the box 204 after actuation of the latching/unlatching device 208.

FIG. 10 shows the arrangement 200 with the module 202 removed from the box 204. A recess 212, into which a substantially flat test field support 214 is slid, is formed on the module 202. The test field support 214 contains a plurality of test sections 250 which can be separated from one another by free spaces 240, provided in the form of prongs. Each test section 250 has a capillary opening 218 for receiving a sample liquid. Light-emitting diodes 216 are located on the upper side of the module 202, each of which is assigned to a test section 250. The test field support 214 is slid into the module 202 in a slot 220 formed on the side surfaces of the recess 212. After the module 202 is extracted from the box 204, the individual capillary openings 218 are freely accessible. The user of the arrangement 200 can therefore select which of the test sections 250 of the test field support 214 to use since use is not restricted to successive presentation of the individual test sections 250.

Figure 11:
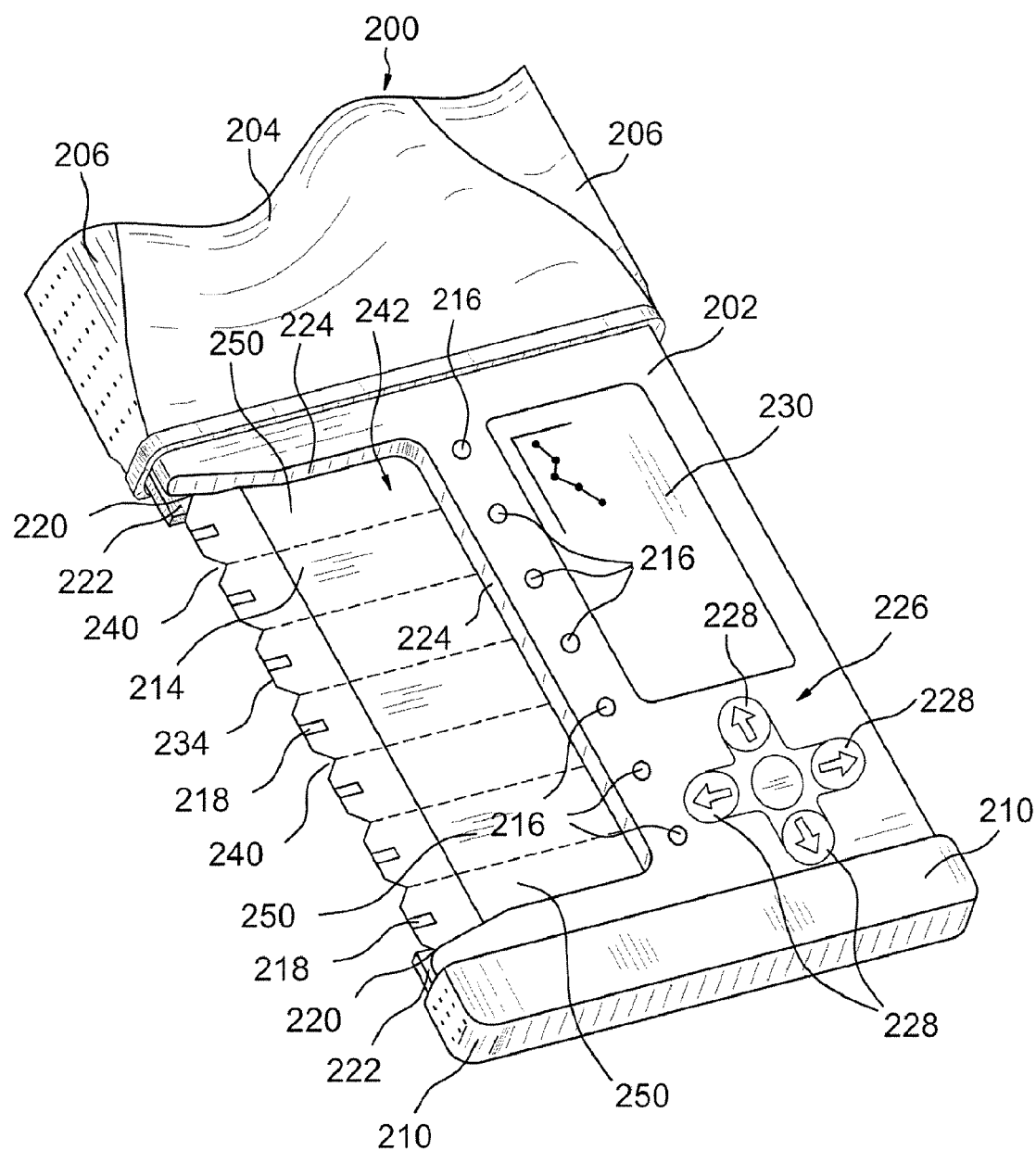
FIG. 11 is a fragmentary perspective view of the module of FIG. 10 with the card-shaped test field support inserted.

As shown in FIG. 11, the module 202 can include a control field 226 having a plurality of buttons 228 on its upper side in the vicinity of the light-emitting diodes 216. The flatly designed test field support 214 can be slid laterally into the module 202 in the recess 212 bounded by a bounding wall 224, its outer edge 234 being freely accessible. Connection of the test field support 214 to the module 202 can be carried out by fully sliding it into the slot 220 of the module using the side opposite from the outer edge 234. Protruding edges of a guide surface 222 below the outer edge 234 of the test field support 214 facilitate the lateral sliding of the test field support 214 into slots 220 which extend perpendicularly to the bounding wall 224. Each test section 250 of the test field support 214 includes a capillary opening 218. The test sections 250 can be separated from one another by, for example, triangularly designed free spaces 240, as noted above. When the test field support 214 is slid laterally into the recess 212 and electrically connected to the module 202 at the end of the slots 220, the user can expose and use the capillary openings 218 arranged on the outer edge 234. The capillary openings 218 can be freely exposed before insertion or sliding into the module 202 by removing a sheet which seals and closes the capillary openings 218. Sealing elements may furthermore be provided on the module 202, with which it is possible to seal the capillary openings 218.

The user can select any of the test sections 250 of the test field support 214. Test field supports 214 can be application-specific by, e.g., providing reagent chemistry that is specific to a particular analyte of interest. Consequently, depending on the particular analyte for which the sample liquid is to be studied, a wide variety of values, such as cholesterol values, lactate values as well as blood sugar values and the like, can be shown in the display 230 by means of the control field 226 and the keypad 280 arranged for viewing by the user.

Figure 12:
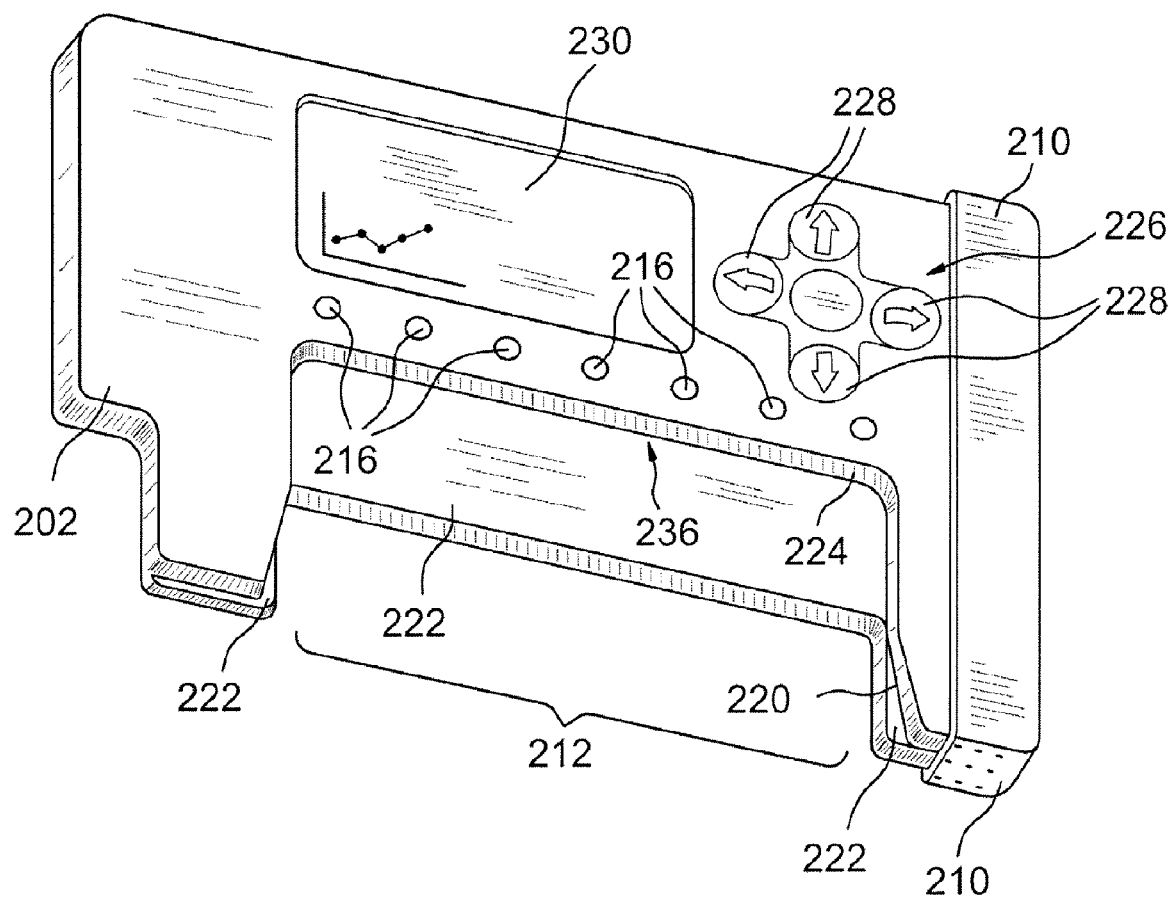
FIG. 12 is a perspective view of the module of FIG. 10 with the card-shaped test field support removed from the module.

FIG. 12 shows module 202 without a test field support 214 slid into the recess 212. A guide surface 222 extends between the slots 220 inside the recess 212. Below the bounding wall 224, the test field support 214 (not shown in FIG. 12) or the test sections 250 formed thereon can be electrically connected in the module 202. The electrical contact region lies below the bounding wall 224 in the module 202 and is indicated by the reference numeral 236. A display 230 is arranged on the upper side of the module 202. Various values can be shown on the display 230 after actuating the keypad 228, for example, values for cholesterol content, lactate, blood sugar and the like.

The displays 24, 150 and 230 of the embodiments described above can furthermore show which of the individual test fields 38 of the respective test field support 26, 100 and 214 have been used and/or which of the individual test fields 68, 104 and 250 are still available for use.

Figure 13:
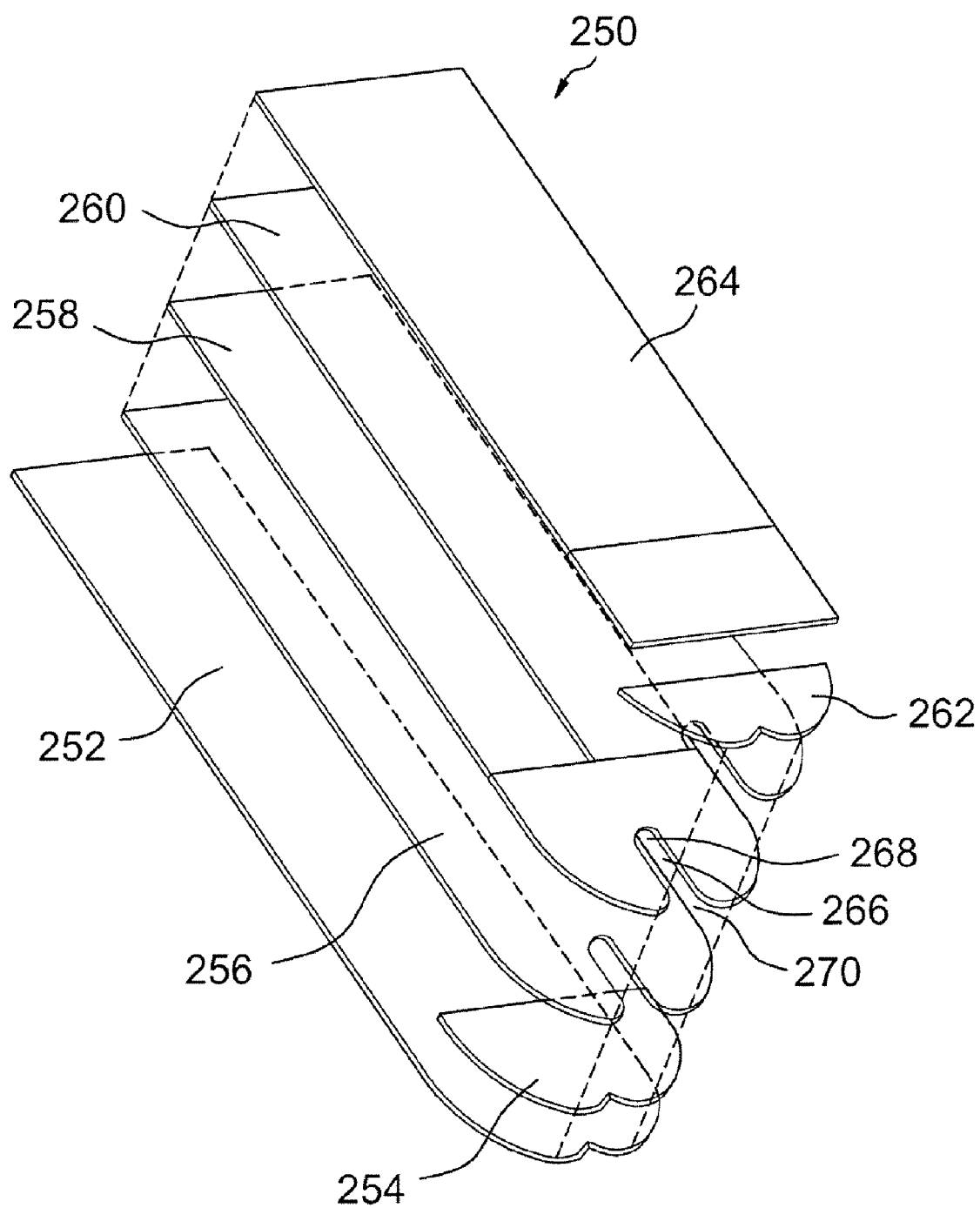
FIG. 13 is an exploded perspective view of a layer arrangement of an individual test strip of the card-shaped test field support.

FIG. 13 shows an exploded representation of a multi-layer test section or test field 250 of a test field support designed in the form of a card. A reagent coating 254 can be applied on a support sheet 252 which can extend to inside the head region of the test section 250. Above or adjacent to the reagent coating 254 there is a first adhesive layer 256 on which a spacer sheet 258 is in turn applied. A second adhesive layer 260 is applied above the spacer sheet 258, and a hydrophilic layer 262 is likewise applied thereto in the head region of the test section 250. A cover layer 264 is applied on top.

A capillary channel 266, the opening of which is denoted by the reference numeral 270, can be formed in the first adhesive layer 256 and the spacer sheet 258 lying above it. For example, a body fluid such as whole blood or plasma can enter the capillary channel 266 at the capillary opening 270 and travel into an electrochemical measuring cell 268 due to the capillary forces acting there. The electrochemical measuring cell 268, which can be formed both in the first adhesive layer 256 and in the spacer sheet 258, is bounded on its upper side by the hydrophilic layer 262 and on its lower side by the reagent coating 254. For economic reasons and in order to save material, the hydrophilic layer 262 and the reagent coating 254 may lie only in the head region of the test section 250, which is part of a card-shaped test field support 214 according to the preceding figures.

FIGS. 14A-14E show the structure of a test field support designed in the form of a card. FIG. 14A shows that the card-shaped test field support 214 can include a plurality of test field sections 250 arranged next to one another. In the representation according to FIG. 14A, the test field support 214 can include five test sections 250 lying next to one another. Each of the test sections 250 includes a capillary opening 270 on an application side 272. As seen in FIG. 14A, these are closed by a separable section of the test field support 214. Electrode terminals for contact with the test field support 214 when it is slid into the slot 220 of the module 202 are included on the contact side 274.

FIG. 14B furthermore shows a test section 250 separated from the test field support 214. In the upper region of the test section 250, the capillary opening 270 is represented as being open, and the capillary channel 266 extends from it to the electrochemical measuring cell 268. The reference numeral 272 denotes the user side on which the capillary opening 270 is also located; the reference numeral 274 denotes the contact side of the test section 250.

FIG. 14C likewise shows a test field support designed in the form of a card, although its contact and application sides are protected. A material projection 276 is included on the application side 272 on the card-shaped test field support 214. The same applies to the contact side 274, on which a material projection 278 is likewise formed. The material projection 276 protects the capillary openings 270 on the application side 272, so as to substantially prevent contaminants from entering the capillary channel 266 before use by the user. The material projection 278 can be used in order to stabilize the contact side 274 of the test field support 214. The material projections 276 and 278 shown in FIG. 14C may, for example, be separated simply by bending them before the test field support 214 is inserted into the slot-in module 202. This can be necessary, on the one hand, in order to electrically connect the test field support 214 designed in the form of a card to the slot-in module 202 and/or in order to permit use of the individual test sections 250 arranged next to one another.

On the contact side 274 of the test field support 214, a material projection 278 can protect the individual electrodes FSE, CE and WE (See FIG. 2) which electronically connect the individual test sections 250 to the module 214 and which can be evaluated according to the analog semiconductor switching matrix 54 of FIG. 3. Reference is made to the description of the electrodes FSE, CE and WE in connection with FIG. 2.

FIG. 14D shows a test field support designed in the form of a card, the application side of which and the contact side of which are exposed. The representation according to FIG. 14D shows the material projection 276 is provided on the application side 272 in FIG. 14C being removed, as indicated by the region identified by the reference numeral 280. The same applies to the removal of the material projection 278 on the contact side 274 of the test field support 214. This provides a multilayer structure 284, reference being made to the exploded representation of FIG. 13. After separation of the material projection 276 on the application side 272, the capillary openings of the capillary channel 266 which connects with the electrochemical measuring cell 268 are open. Such openings can be activated by wetting with a body fluid such as whole blood or plasma. FIG. 14E furthermore shows an individual test section 250, in which the capillary opening 270 and the electrodes FSE, CE and WE have been exposed by separating the material projections 276 and 278 (compare FIG. 14C).

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 10 measuring device
12 lower shell
14 upper shell
16 articulated connection
18 folding case
20 cavity boundary
21 cavity or recess
22 $1^{st}$ display
24 $2^{nd}$ display
26 flat test field support
28 test field support surface
30 test field array
32 base sheet
34 support sheet
36 conductor tracks
38 electrodes
CE counter electrode
WE wettable electrode
FSE $1^{st}$ filling level electrode
FSE $2^{nd}$ filling level electrode
40 reagent layer
42 spacer sheet
44 hole
46 measuring chamber/measuring capillary space
48 cover sheet
50 hydrophilic layer
52 vent
54 analog semiconductor switching matrix
56 CE terminal
58 WE terminal
60 terminal of $1^{st}$ FSE
62 terminal of $2^{nd}$ FSE
64 $1^{st}$ switch
66 $2^{nd}$ switch
68 individual test field
70 electrical contact strip
72 shell-side electrical contact strip
74 closed individual test field
76 ring-pull closure
78 cover
80 reception well (sample receiving well)
82 sealing edge
100 capillary sensor support
102 $1^{st}$ long side
104 capillary sensor
106 $2^{nd}$ long side
108 capillary with opening
110 $1^{st}$ contact region of capillary sensor support
112 $2^{nd}$ contact region of capillary sensor support
140 measuring and analysis device
142 lower part
144 upper part
146 hinge
148 resilient contacts arranged in a row
150 display
152 control buttons
154 cover sleeve
156 retracted state
158 slid-on state
200 slot-in arrangement
202 slot-in module
204 slot-in box (cover)
206 gripping piece
208 latching/unlatching
210 gripping side
212 recess
214 test field support
216 light-emitting diodes
218 capillary opening
220 slot-in slot
222 guide surface
224 bounding wall
226 control field
248 keypad
230 display
234 edge of test field support
236 contact region of test field support 214
238 latching element
240 free space 242 slot-in position of test field support 214
250 test section
252 support sheet
254 reagent coating
256 1$^{st}$ adhesive layer
258 spacer sheet
260 2$^{nd}$ adhesive layer
262 hydrophilic layer
264 cover layer
266 capillary channel
268 measuring chamber
270 capillary opening
272 application side
274 contact side
276 material projection on application side
278 material projection on contact side
280 extent of detached material projection 276
282 extent of detached material projection 278
284 layer structure of test section

What is claimed is:

1. A measuring device for analyzing a sample liquid for presence or concentration of at least one analyte, comprising:
 a measuring device body having an open position and a closed position;
 evaluation electronics;
 a test field support housed in the measuring device and coupled to the evaluation electronics, the test field support including a plurality of test fields, each test field of the plurality being accessible to a user when the measuring device body is in the open position;
 each one of the plurality of test fields comprising an electrochemical measuring cell having a pair of sample sufficiency electrodes and a reagent adapted to react with a sample liquid to produce a response that is measurable by the evaluation electronics;
 wherein the evaluation electronics are adapted to determine which one of the plurality of test fields has been wetted with the body fluid sample; and
 wherein the device selectively provides visual indicia indicating which test fields of the plurality of test fields have been used and which remain unused.

2. The measuring device of claim 1, wherein the test field support is removably housed in the measuring device, whereby the test field support is replaceable.

3. The measuring device of claim 2, wherein each one of the plurality of test fields comprises at least one set of electrodes which electrically connect to the evaluation electronics upon insertion of the test field support in the measuring device.

4. The measuring device of claim 2, wherein the positions of the test fields on the test field support are fixed relative to the measuring device when the test field support is positioned in the measuring device.

5. The measuring device of claim 2, wherein the measuring device body comprises an upper shell and a lower shell, at least one of the upper shell and lower shell including an electrical contact to connect with a corresponding electrical contact of the test field support, and at least one of the upper shell and lower shell including a display for displaying a test result.

6. The measuring device of claim 1, wherein the test field support comprises multiple layers sandwiched together which cooperate to define the plurality of electrochemical measuring cells.

7. The measuring device of claim 1, wherein the plurality of test fields comprises a plurality of capillary sensors positioned side by side.

8. The measuring device of claim 1, wherein the plurality of test fields is arranged on the test field support in a matrix.

9. The measuring device of claim 1, further comprising a plurality of removable covers wherein each one of the plurality of test fields includes a sample reception well and wherein a separate one of the removable covers is configured to individually seal each of the sample reception wells.

10. The measuring device of claim 1, wherein the measuring device body comprises a module having a slot, a cover having an opening to removably receive the module, and a latch which can be triggered to allow removal of the module from the cover.

11. The measuring device of claim 1, wherein the test field support is removably and replacably receivable in the measuring device body, the test field support including an electrical contact which is connectable to a corresponding electrical contact carried by the measuring device body; and
 the test field support comprising multiple layers sandwiched together which cooperate to define the plurality of electrochemical measuring cells each of the electrochemical measuring cells having a sample receiving opening and a capillary channel configured to draw a liquid sample therein, each one of the plurality of test fields comprising a respective one of the electrochemical measuring cells.

12. The measuring device of claim 11, wherein the multiple layers include a base layer having a plurality of electrode sets thereon and a reagent layer at least partially covering each electrode set, each electrode set being positioned in a respective one of the plurality of electrochemical measuring cells.

13. The measuring device of claim 12, wherein the base layer defines each pair of sample sufficiency electrodes thereon, each pair of sample sufficiency electrodes being positioned in a respective one of the plurality of electrochemical measuring cells.

14. The measuring device of claim 12, wherein the multiple layers further comprise a spacer layer overlying the base layer and a cover layer overlying the spacer layer.

15. The measuring device of claim 11, wherein each one of the test fields of the plurality of test fields comprises a sample reception well in communication with each respective electrochemical measuring cell, each sample reception well having a removable cover configured to seal the sample reception well.

16. The measuring device of claim 11, wherein the positions of the test fields on the test field support are fixed relative to the measuring device when the test field support is received in the measuring device.

17. The measuring device of claim 11, wherein the measuring device body comprises an upper shell and a lower shell, at least one of the upper shell and lower shell including an electrical contact to connect with a corresponding electrical contact of the test field support, and at least one of the upper shell and lower shell including a display for displaying a test result.

18. The measuring device of claim 1 further comprising a display wherein the visual indicia are presented on the display.

19. The measuring device of claim 1 wherein the selective provision of visual indicia indicating which test fields of the plurality of test fields have been used and which remain unused is determined by the evaluation electronics based upon the determinations of which one of the test fields have been wetted with the body fluid sample performed by the evaluation electronics.

20. The measuring device of claim 19 wherein the evaluation electronics repeatedly evaluate if the test fields have been wetted and the selective provision of visual indicia indicating which test fields of the plurality of test fields have been used and which remain unused is based upon the repeated evaluations performed by the evaluation electronics.

21. A method for determining presence or concentration of at least one analyte in a body fluid sample using a measurement device having a display, evaluation electronics, and a plurality of test fields provided on a test field support, the method comprising:
  (a) opening the measurement device to provide simultaneous access to each one of the plurality of test fields;
  (b) selecting one of the test fields from the plurality of test fields;
  (c) depositing the body fluid sample on the selected test field;
  (d) drawing the sample into an electrochemical cell of the selected test field;
  (e) using the evaluation electronics to determine which one of the plurality of test fields has been wetted with the body fluid sample;
  (f) analyzing the sample using the evaluation electronics;
  (g) displaying on the display a result indicative of the presence or concentration of the analyte in the body fluid sample;
  (h) providing visual indicia with the measuring device of which test fields of the plurality of test fields have been used or remain unused;
  (i) closing the measurement device without exhausting all of the plurality of test fields; and
  (j) repeating steps (a) through (h) with a second one of the test fields.

22. The method of claim 21, wherein each one of the test fields comprises a set of sample sufficiency electrodes, the method further comprising measuring an electrical parameter through or across each set of sample sufficiency electrodes.

23. The method of claim 21, further comprising repeating steps (a)-(h) until each of the test fields have been used.

24. The method of claim 23, further comprising:
  removing the test field support from the measuring device;
  inserting a new test field support in the measuring device; and
  repeating steps (a)-(i) using the new test field support.

25. The method of claim 21, wherein the measurement device includes a plurality of removable covers with each one of the plurality of test fields having a separate one of the plurality of removable covers associated therewith and wherein the method further comprising, before step (c), removing the cover that seals the selected test field and replacing the cover after step (c).

26. The method of claim 21 wherein the visual indicia are presented on the display.

27. The method of claim 21 wherein the step of providing visual indicia comprises using the evaluation electronics to determine which of the test fields have been used and which remain unused based upon determinations made by the evaluation electronics of which one of the plurality of test fields have been wetted.

28. The method of claim 21 wherein the method further comprises using the evaluation electronics to repeatedly determine if any of the test fields have been wetted and wherein the step of providing visual indicia comprises using the evaluation electronics to determine which of the test fields have been used and which remain unused based upon determinations made by the evaluation electronics of which one of the plurality of test fields have been wetted.

* * * * *